(12) United States Patent
Pein

(10) Patent No.: US 7,651,486 B2
(45) Date of Patent: Jan. 26, 2010

(54) SURGICAL DEVICE FOR REMOVING TISSUE CELLS FROM A BIOLOGICAL STRUCTURE

(75) Inventor: Andreas Pein, Einhaus (DE)

(73) Assignee: Human Med AG, Schwerin (DE)

( * ) Notice: Subject to any disclaimer, the term of this patent is extended or adjusted under 35 U.S.C. 154(b) by 656 days.

(21) Appl. No.: 10/520,209

(22) PCT Filed: Jul. 7, 2003

(86) PCT No.: PCT/DE03/02256

§ 371 (c)(1),
(2), (4) Date: Dec. 28, 2005

(87) PCT Pub. No.: WO2004/004788

PCT Pub. Date: Jan. 15, 2004

(65) Prior Publication Data

US 2006/0155243 A1     Jul. 13, 2006

(30) Foreign Application Priority Data

Jul. 9, 2002   (DE) .......................... 202 10 646 U

(51) Int. Cl.
*A61M 1/00* (2006.01)
(52) U.S. Cl. ................ 604/355; 604/19; 604/21; 604/27; 604/35; 604/48; 604/73; 604/317; 604/327; 604/540
(58) Field of Classification Search .......... 604/19, 604/21, 27, 35, 48, 73, 317, 327, 540, 542
See application file for complete search history.

(56) References Cited

U.S. PATENT DOCUMENTS

| | | | | |
|---|---|---|---|---|
| 5,236,414 A | * | 8/1993 | Takasu | ........................ 604/22 |
| 5,242,387 A | | 9/1993 | Loughlin | |
| 5,499,970 A | | 3/1996 | Olson | |
| 5,573,504 A | | 11/1996 | Dorsey, III | |
| 5,759,178 A | | 6/1998 | Wells | |
| 5,836,909 A | | 11/1998 | Cosmescu | |
| 5,911,700 A | * | 6/1999 | Mozsary et al. | ................ 604/22 |
| 5,944,686 A | * | 8/1999 | Patterson et al. | .............. 604/22 |
| 6,817,996 B2 | * | 11/2004 | Fard et al. | .................... 604/542 |
| 7,063,713 B1 | * | 6/2006 | Butsch et al. | ................ 606/167 |

FOREIGN PATENT DOCUMENTS

| | | | |
|---|---|---|---|
| DE | 100 33 278 A1 | | 1/2002 |
| FR | 2700958 | * | 2/1993 |
| FR | 2 700 958 A1 | * | 8/1994 |
| WO | WO 03/039629 | | 5/2003 |

* cited by examiner

*Primary Examiner*—Tatyana Zalukaeva
*Assistant Examiner*—Ilya Y Treyger
(74) *Attorney, Agent, or Firm*—Norris McLaughlin & Marcus, PA; Christa Hildebrand, Esq.

(57) ABSTRACT

The invention allows an increase in scope of application of a surgical device wherein the operational handpiece is embodied in the form of two parts, one of which includes a handpiece with an injection cannula and the other being a complementary part. The complementary part includes a stabilization handle and can be placed onto the injection cannula in addition to being able to be fixed to the handpiece of the operational handpiece.

4 Claims, 2 Drawing Sheets

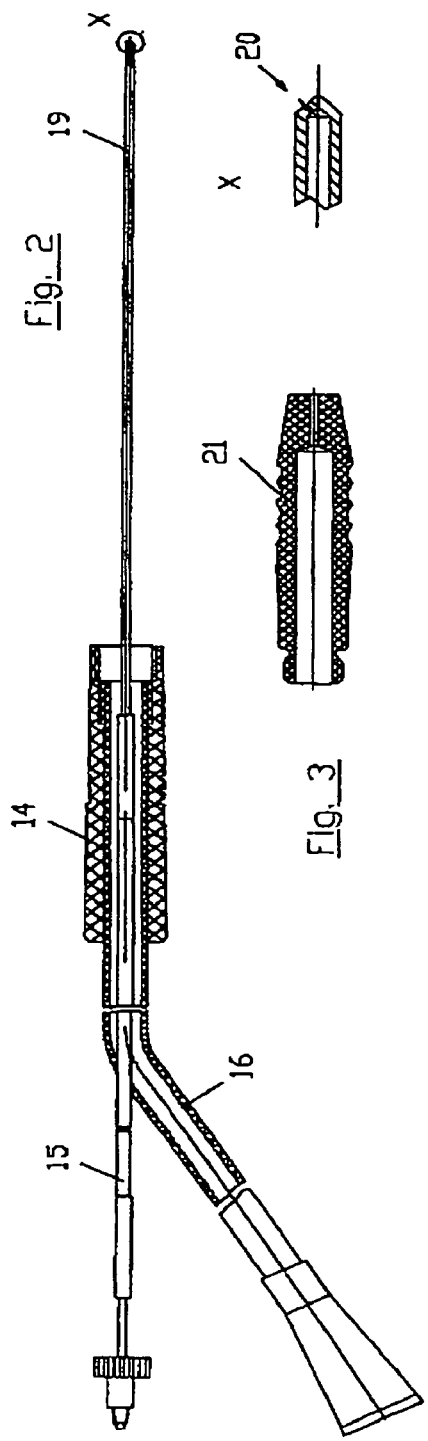
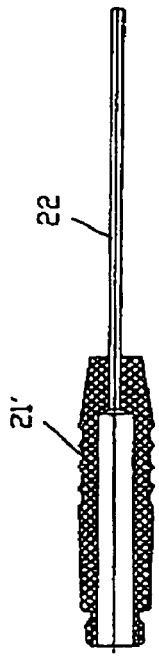
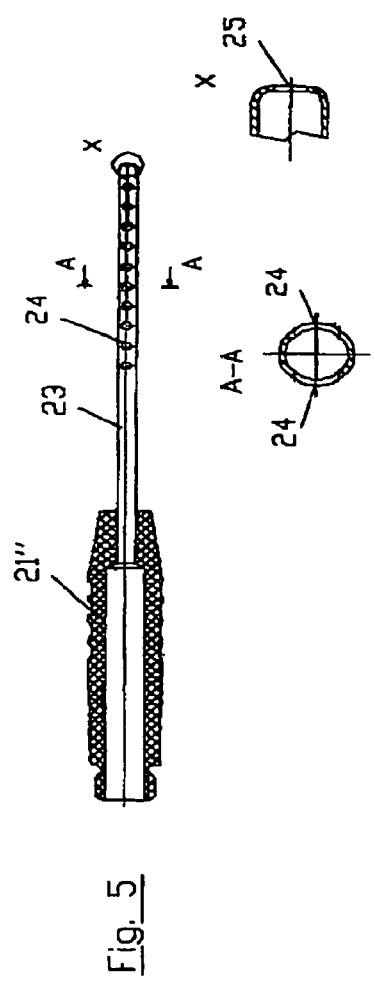
Fig. 2  Fig. 3  Fig. 4  Fig. 5

SURGICAL DEVICE FOR REMOVING TISSUE CELLS FROM A BIOLOGICAL STRUCTURE

BACKGROUND OF THE INVENTION

1) Field of the Invention

The invention relates to a surgical device for injecting a fluid and/or for removing tissue cells from a biological body or structure, including a supply device having a fluid jet unit for injecting a separation fluid or a process fluid and/or including a suction device for suctioning off separated or dissolved tissue cells and/or the separation fluid or the process fluid, and a surgical hand piece with an inner injection cannula and an outer suction tube, both of which form an annular suction channel in the region of the surgical hand piece. The outer suction tube is adapted to be placed on the injection cannula and to be secured to the surgical hand piece. The injection cannula includes a front nozzle opening and the suction tube includes a plurality of suction bores distributed along its periphery. Such device and instrument is used in surgical clinical settings to suction off fatty tissue for health and cosmetic reasons. Such device and instrument is also used for removing vital tissue cells, for example from the liver, for the purpose of reproducing these tissue cells through cell division and then inserting the tissue cells in the same or in a different biological body or structure.

2) Description of the Related Art

A number of methods and devices are known that can achieve this goal.

For example, DE 299 14 230 U1 describes a cannula for suctioning off fatty tissue, with the cannula formed as a tube that has one closed end and an other open end that is connected by an adapter to a suction device. The tube includes several suction openings distributed along the periphery, with the size of the openings adapted to the size of the fatty tissue cells.

The cannula is pierced into the corresponding tissue layers and is continuously moved back and forth during the procedure. Through the force generated by the vacuum and with support of the mechanical force of the moving cannula, tissue cells are destructively torn away and then suctioned off. This method is very stressful for the patient and is therefore only rarely used in practice.

It is known to reduce the stress by injecting, in a separate process step before the surgical procedure, a process fluid into the affected tissue to dissolve the tissue cells, which can then be more effectively and more easily suctioned off. The injected process fluid together with the dissolved tissue cells are suctioned off through the suction tube.

DE 200 09 786 U1 describes a device for suctioning off fatty tissue, which functionally combines the two aforedescribed process steps, i.e., injecting the tissue-dissolving process fluid and suctioning off the dissolved tissue cells. For this purpose, an interior injection line for the tissue-dissolving process fluid is arranged in the suction cannula, with the exit opening of the injection line disposed on the distal end of the suction cannula and connected to a process fluid pump. In this way, process fluid is injected continuously and suctioned off together with the fatty tissue cells. This makes the process more continuous and shortens the duration of the surgical procedure.

Disadvantageously, however, the aforementioned technical solutions have in common that they destroy not only the fatty tissue cells, but also adjacent tissue cells, such as blood cells. This can harm the human body and complicate and prolong the healing process. These technical solutions are therefore not suitable for removing healthy tissue cells for further use.

DE 100 33 278 A1 describes a surgical device for removing tissue cells from a biological structure that obviates this disadvantage. This device includes a water jet unit with a pressure generator and an injection cannula emitting a separation water jet under pressure, and a suction device that includes a suction pump and a suction tube with the suction openings distributed along the periphery, through which the separated tissue cells are discharged together with the used water. The injection cannula for the emitted water jet is arranged in the interior of the suction tube, with both the cannula and the suction tube combined in a hand piece that can be interchanged via a screw-in adapter.

The exit opening of the injection cannula has a crosssection and the exiting water jet a pressure suitable to cause the water jet to exert a peeling effect.

The water jet is able to cut through or separate tissue parts. However, the tissue cells are not destroyed, because due to the curved surface and the pliability of the tissue cells, the water jet does not experience any resistance and is therefore not deflected in its effective direction. As a result, the water jet finds its way between the tissue cells in an intelligent manner, until it meets resistance essential for developing a separation force, thereby urging the adjacent tissue cells apart and separating them, without destroying them. Because the selection is gentle, there is no need to inject a process fluid for dissolving the tissue cells, as was required in the prior art.

The relatively large number of applications and the large number of implementations of such hand piece, due to the different required diameters, and the desired high utilization rate for the entire apparatus make it necessary to have a large number of hand pieces available with different lengths, different diameters of the suction tube, and different suction openings in the suction tube. This large number of tools makes the entire unit unduly expensive.

Moreover, many situations require application of an anesthetic before the surgical procedure, which necessitates special injection instruments. This further increases the cost of the surgical procedure and the conversion time from the injection unit to the tissue removal unit, and vice versa.

It is therefore an object of the invention to develop a device of the aforedescribed type for removal of tissue cells, which can be used universally for anesthesia and for tissue removal and which has a simple design and is easy to operate.

BRIEF SUMMARY OR THE INVENTION

This object is solved utilizing a surgical hand piece which is implemented in two parts, with a first part comprising a hand piece with a injection cannula and a second part comprising a complementary part that can be placed onto the injection cannula and which is configured for attachment to the hand piece of the surgical hand piece. Further embodiments are recited in the dependent claims. The novel surgical device eliminates the aforementioned disadvantages of the state of the art.

The particular advantage of the novel surgical device is its universal applicability. The basic configuration, which includes the handle and the injection cannula, can be provided with a variety of complementary parts and hence be adapted to the respective specific application. The complementary parts can be easily and quickly exchanged, which saves significantly time in the operating theater.

Considerable expenditures for the device and setup can be saved by requiring only a single supply device, so that no longer complete surgical hand pieces need to be exchanged for the different applications, but instead only the various complementary parts. This also saves time during surgery.

The invention will now be described with reference to an exemplary embodiment.

It is shown in:

BRIEF DESCRIPTION OF THE DRAWINGS

FIG. 2 a basic configuration of the surgical hand piece with the detail X;

FIG. 3 a first complementary part in form of a stabilizing handle for the injection cannula;

FIG. 4 a second complementary part in form of a stabilizing handle with a stabilizing tube; and FIG. 5 a third complementary part in form of a stabilizing handle with a suction tube and the details X and A-A.

DETAILED DESCRIPTION OF THE INVENTION

Figure 1:
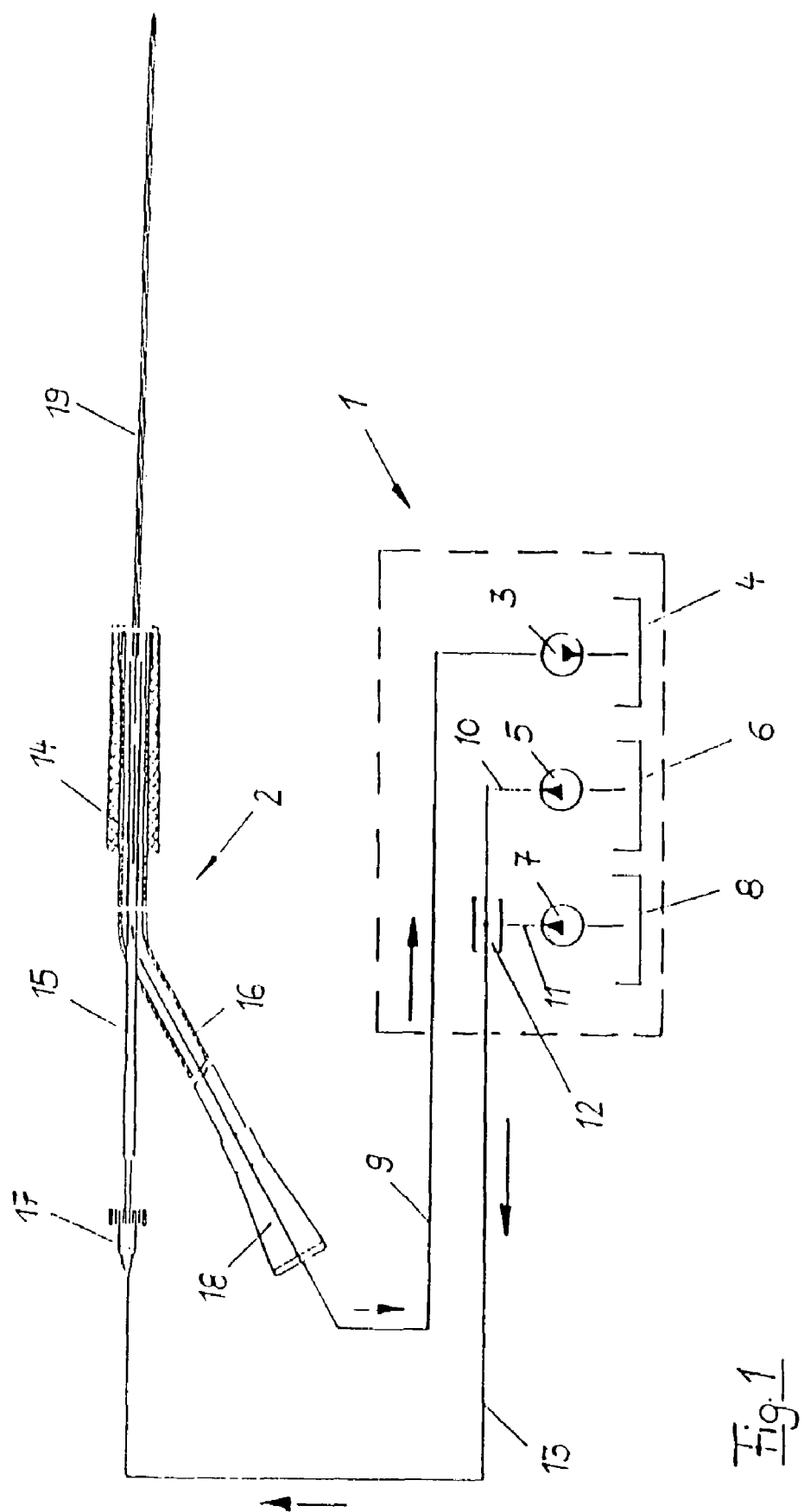
FIG. 1 a simplified schematic diagram of the novel surgical device.

As seen in FIG. 1, the surgical device includes a supply unit 1 and a surgical hand piece 2. The supply unit 1 includes a vacuum pump 3 with a receptacle container 4, a supply pump 5 with a supply container 6 for a sterile separation fluid that can be formed into a jet, and a supply pump 7 with a supply container 8 for an anesthetic or another process fluid.

The vacuum pump 3 is connected via a vacuum line 9 with the surgical hand piece 1. Conversely, the two supply pumps 5 and 7 each have respective pressure lines 10 and 11, with both pressure lines 10, 11 terminating at a switchable distribution valve 12. The distribution valve 12 is provided to enable alternative use of the two supply pumps 5 and 7, and is connected on the consumption side with the surgical hand piece 1 via a pressure supply line 13.

The surgical hand piece 1 includes, as also shown in greater detail in FIG. 2, a hand piece 14 with an interior injection line 15 and a suction line 16 that surrounds the injection line 15. The injection line 15 emerges from the suction line 16 on the proximal side of the hand piece 14 and is connected with the pressure supply line 13 via a coupler 17, whereas the suction line 16 is connected to the vacuum line 9 with a coupler 18. A stationary injection cannula 19 that is connected with the injection line 15 is located on the distal side of the hand piece 14. The free end of the injection cannula 19 is formed as a conically tipped injection nozzle and preferably has a nozzle opening 20 formed as a slit and disposed on the conical surface. Because of this configuration of the nozzle opening 20 on the conical surface, the fluid jet exits in a direction different from the axis of the injection cannula 19. The nozzle opening 20 is sized so that, for a selected pressure in the pressure supply line 13, a substantially flat fluid jet exits which exerts a peeling separation effect on the tissue cells.

The length of the injection cannula 19 can be adapted to reach also the deeper tissue regions.

FIG. 3 shows a first complementary part for stabilizing the injection cannula 19 for injecting an anesthetic. Since the relatively long and thin injection cannula 19 is not dimensionally stable, but only a relatively shallow puncture depth is required for injecting an anesthetic, the complementary part in the depicted embodiment consists of a stabilizing handle 21 that is placed onto the injection cannula 19 and screwed into the hand piece 14. This arrangement increases the guided and supported length on the hand piece 14. For ergonomic reasons, the stabilizing handle 21 and the hand piece 14 have the same outside dimensions and a complementary design.

FIG. 4 shows another complementary part which includes a stabilizing handle 21' and an attached stabilizing tube 22 that supports the injection cannula 19 over its entire length. The free end of the injection cannula 19 is open and has a suitable length, so that a sufficiently long section of the nozzle opening 20 of the injection cannula 19 protrudes from the stabilizing tube 22. The stabilized injection cannula 19 can be used to apply an anesthetic or another process fluid to deeper tissue layers.

Finally, FIG. 5 shows a complementary part with a stabilizing handle 21" and an attached suction tube 23. The suction tube 23 is dimensioned so as to encompass the injection cannula 19 and to form in conjunction with the injection cannula 19 an interior annular suction channel. Several suction bores 24 distributed about the periphery of the suction tube 23 terminate in the annular suction channel. An axial bore 25 with a diameter that conforms with clearance to the diameter of the injection camera 19, is arranged on the distal end of the suction tube 23. Moreover, the suction tube 23 has a suitable length so that a sufficiently long section of the nozzle opening 20 of the injection cannula 19 protrudes from the axial bore 25.

The novel surgical device for removing tissue cells can be used universally and replaces a large number of special tools.

For example, the surgical device for injecting an anesthetic can be used in the same manner as is typical before tissue removal. For this procedure, if required, the first complementary part in form of the stabilizing handle 21 or the second complementary part in the form of the stabilizing handle 21' with the stabilizing tube 22 is initially placed onto the injection cannula 19 and connected with the hand piece 14. The distribution valve 12 of the supply unit 1 is then switched to a position where the supply pump 7, for example for the anesthetic, is connected with the injection line 15 via the pressure supply line 13. When the injection cannula 19 has entered the corresponding tissue part, the supply pump 7 is activated and a pre-measured quantity of anesthetic is injected.

The novel surgical device with the same configuration of the surgical hand piece 2 can also be used for injecting a process fluid, for example, for dissolving tissue cells in advance. The distribution valve 12 is then switched to a position, where the pressure supply line 13 is connected with a supply container containing a corresponding tissue-dissolving process fluid.

However, the novel surgical device is primarily used for removal of excess fatty tissue or of tissue cells that can reproduce. For this application, the third complementary part in the form of the stabilizing handle 21" with the suction tube 23 is placed over the injection cannula 19 and connected with the hand piece 14 of the surgical hand piece 1. The distribution valve 12 is switched to a position where the pressure supply line 13 is connected with the supply pump 5 for the sterile separation fluid 6.

After the suction tube 23 with the complementary injection cannula 19 has been inserted in the corresponding tissue layer, the supply pump 5 for the separation fluid and the vacuum pump 3 are turned on, whereby the pumping capacity of the two pumps 3, 5 is matched. The separation fluid then exits the nozzle opening 20 of the injection cannula 19 as a flat jet that is directed away from the axial direction, and is deflected in an intelligent manner into the gaps between the tissue cells. As a result, the tissue cells are not exposed to the separation force, but are instead only urged apart and separated. The tissue cells peeled away in this manner are simultaneously suctioned off together with the consumed separation fluid by vacuum force and transported through the suction bores 24, the inner annular suction channel and the suction line 16 of the surgical hand piece 2 and through the vacuum line 9 into the receptacle container 4. From there, the collected tissue cells are disposed of or sorted for further processing, as required.

LIST OF REFERENCE CHARACTERS 1 supply device
2 surgical hand piece
3 vacuum pump
4 receptacle container
5 supply pump
6 supply container for a sterile separation fluid
7 supply pump
8 supply container for an anesthetic or a process fluid
9 vacuum line
10 pressure line
11 pressure line
12 switchable distribution valve
13 pressure supply line
14 hand piece
15 injection line
10 suction line
17 coupler
18 coupler
19 injection cannula
20 nozzle
21 stabilizing handle
22 stabilizing tube
23 suction tube
24 suction bore
25 axial bore

The invention claimed is:

1. A surgical device for injecting a fluid and/or for removing tissue cells from a biological structure, comprising
    (a) a supply device (1) including a vacuum pump (3), and a supply pump (5, 7) for injecting a separation fluid or a process fluid and for suctioning off separated or dissolved tissue cells and/or the separation fluid or the process fluid, and
    (b) a surgical hand piece (2) with an inner injection cannula (19) and an outer suction tube (23), both of which form an annular suction channel in the region of the surgical hand piece (2), wherein the outer suction tube (23) is adapted to be placed on the injection cannula (19) and to be secured to the surgical hand piece (2), and wherein the injection cannula (19) includes a front nozzle opening (20) and the suction tube (23) includes a plurality of suction bores (24) distributed along its periphery, and
    wherein the surgical hand piece (2) is provided with a handle (14) and the suction tube (23) is configured with a handle (21") to form a complementary part, wherein the outside dimensions of the handle (14) of the surgical hand piece (2) are adapted to those dimensions of the handle (21") of the suction tube (23), and wherein the handle (14) of the surgical hand piece (2) is configured to be connectable with the handle (21") of the suction tube (23) or optionally with another complimentary part that also includes an adapted handle (21, 21'), wherein the suction tube (23) has a front axial bore (25) that matches with clearance the diameter of the injection cannula (19) and the length of the suction tube (23) is shorter than the length of the injection cannula (19) by a sufficient amount, so that the tip of the injection cannula (19) with the nozzle opening (20) protrudes by a sufficient length.

2. The surgical device according to claim 1, wherein another complementary part comprises a stabilizing handle (21) for stabilizing the injection cannula (19).

3. The surgical device according to claim 1, wherein another complementary part comprises a handle (21') and an open stabilizing tube (22), wherein the inner diameter of the stabilizing tube (22) matches with clearance the outer diameter of the injection cannula (19) and the length of the stabilizing tube (22) is shorter than the length of the injection cannula (19) by a sufficient amount, so that the tip of the injection cannula (19) with the nozzle opening (20) protrudes by a sufficient length.

4. The surgical device according to claim 1, wherein for alternatively supplying the injection cannula (19) with different process fluids, the fluid jet unit of the supply device (1) is provided with one or more supply pumps (5, 7), and with a switchable directional control valve (12).

* * * * *